United States Patent
Nadeau et al.

(10) Patent No.: US 9,128,023 B2
(45) Date of Patent: Sep. 8, 2015

(54) CALIBRATION SCHEME FOR GAS ABSORPTION SPECTRA DETECTION

(71) Applicant: TEXAS INSTRUMENTS INCORPORATED, Dallas, TX (US)

(72) Inventors: Phillip Michel Nadeau, Cambridge, MA (US); Baher S. Haroun, Allen, TX (US); Srinath M. Ramaswamy, Murphy, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 272 days.

(21) Appl. No.: 13/916,273

(22) Filed: Jun. 12, 2013

(65) Prior Publication Data
US 2014/0368376 A1    Dec. 18, 2014

(51) Int. Cl.
G01S 7/40 (2006.01)
G01N 22/00 (2006.01)
G01J 3/28 (2006.01)
G01S 7/41 (2006.01)
G01J 3/42 (2006.01)
G01S 7/00 (2006.01)

(52) U.S. Cl.
CPC . *G01N 22/00* (2013.01); *G01J 3/28* (2013.01); *G01J 3/42* (2013.01); *G01S 7/40* (2013.01); *G01S 7/41* (2013.01)

(58) Field of Classification Search
CPC ............ G01N 22/00; G01S 7/02; G01S 7/40; G01S 7/4008; G01S 7/4021; G01S 7/41; G01S 7/411; G01S 7/412; G01S 7/48; G01S 7/4802; G01S 7/497; G01S 13/02; G01S 13/88; G01J 3/00; G01J 3/02; G01J 3/28; G01J 3/42

USPC ............ 342/89, 90, 165–175, 192–197, 350, 342/351, 22; 73/1.01, 1.02, 1.06, 23.2; 324/76.11, 76.12, 76.13, 76.14, 324/76.19–76.37, 600, 629, 637, 639, 642, 324/633, 636; 356/300, 326, 51, 302, 303, 356/311, 316, 450, 451, 454; 250/253, 256, 250/269.1, 269.6, 269.8, 281, 282, 200, 250/216, 221

See application file for complete search history.

(56) References Cited

U.S. PATENT DOCUMENTS

| | | | | |
|---|---|---|---|---|
| 2,602,835 A | * | 7/1952 | Hershberger | 324/636 |
| 2,637,767 A | * | 5/1953 | Hershberger | 324/636 |
| 2,867,781 A | * | 1/1959 | Tomiyasu | 324/639 |
| 2,882,493 A | * | 4/1959 | Dicke | 324/633 |
| 3,456,185 A | * | 7/1969 | Shuzo et al. | 324/636 |
| 3,562,631 A | * | 2/1971 | Lee et al. | 324/636 |
| 3,784,938 A | * | 1/1974 | Cuthbert et al. | 356/316 |
| 3,866,118 A | * | 2/1975 | Ghosh et al. | 324/639 |
| 3,889,182 A | * | 6/1975 | Easley et al. | 324/636 |
| 3,973,186 A | * | 8/1976 | Uehara et al. | 324/636 |
| 4,029,416 A | * | 6/1977 | Hawes | 356/51 |

(Continued)

*Primary Examiner* — Bernarr Gregory
(74) *Attorney, Agent, or Firm* — John R. Pessetto; Charles A. Brill; Frank D. Cimino

(57) ABSTRACT

A technique for removing the background from a transmission spectrum including determining performance characteristics of a detector, measuring a transmission spectrum that includes an absorption line, determining performance characteristics of a gas cell, and removing a background spectrum from the transmission spectrum by combining the transmission spectrum with the performance characteristics of the detector and the performance characteristics of the gas cell.

23 Claims, 2 Drawing Sheets

(56) References Cited

U.S. PATENT DOCUMENTS

| | | | |
|---|---|---|---|
| 4,054,384 A * | 10/1977 | Hawes | 356/51 |
| 4,390,783 A * | 6/1983 | Grau | 250/269.8 |
| 4,607,521 A * | 8/1986 | Saito et al. | 73/23.2 |
| 4,972,699 A * | 11/1990 | Berger et al. | 73/23.2 |
| 5,548,217 A * | 8/1996 | Gibson et al. | 324/636 |
| 5,672,869 A * | 9/1997 | Windig et al. | 250/282 |
| 6,525,312 B1 * | 2/2003 | Cousins | 250/282 |
| 7,057,398 B2 * | 6/2006 | Zhu et al. | 324/639 |
| 7,248,370 B2 * | 7/2007 | Jones | 356/454 |
| 7,251,037 B2 * | 7/2007 | Jones | 356/454 |
| 8,117,010 B2 * | 2/2012 | Busch et al. | 356/303 |
| 8,304,719 B2 * | 11/2012 | Wang et al. | 250/282 |
| 2005/0285023 A1 * | 12/2005 | Liu | 250/221 |

* cited by examiner

CALIBRATION SCHEME FOR GAS ABSORPTION SPECTRA DETECTION

CROSS-REFERENCE TO RELATED APPLICATION

The present application may be related to co-pending U.S. patent application Ser. No. 13/900,668, filed May 23, 2013; Ser. No. 13/916,331, filed Jun. 12, 2013; and Ser. No. 13/926,516, filed Jun. 25, 2013.

BACKGROUND

Spectroscopy and spectrometers may be used as various measurement and reference tools. Such tools may use an array of measurement techniques on just about any form of matter. The measurement techniques may depend on the material of interest, which may dictate what frequency/wavelength may be best suited for the measurements. Spectrometers, for example, may be suited to measure emission or absorption spectrums. Further, absorption spectrometers may specifically look for characteristic absorption lines of the material. The absorption lines may be used to identify an unknown substance from a catalogue of known spectrums, or the absorption line may be used to detect the amount of a known substance in a sample. In general, spectroscopy principles may be used for various measurements or to define a reference based on frequency or wavelength.

SUMMARY

A technique for removing the background from a transmission spectrum including determining performance characteristics of a detector, measuring a transmission spectrum that includes an absorption line, determining performance characteristics of a gas cell, and removing a background spectrum from the transmission spectrum by combining the transmission spectrum with the performance characteristics of the detector and the performance characteristics of the gas cell.

A system for removing a background spectrum from a measured spectrum that includes an absorption cell containing a gas, a radio frequency (RF) transmitter to transmit a RF signal through the absorption cell, a detector to receive the RF signal, and a control module coupled to the transmitter and the detector. The control module to estimate performance characteristics of the detector and performance characteristics of the gas cell, measure a transmission spectrum of the gas in the absorption cell, and combine the transmission spectrum with the performance characteristics of the gas cell and the detector to remove a background spectrum from the transmission spectrum.

A spectrometer that includes an absorption cell containing a gas, a radio frequency (RF) transmitter to transmit RF signals into the absorption cell, a RF receiver to receive the RF signals, and a RF signal generation and detection module coupled to the transmitter and the receiver. The RF signal generation and detection module is to generate the RF signals, detect the RF signals received by the receiver, and measure a transmission spectrum based on the received RF signals, wherein the measured transmission spectrum includes an absorption line of the gas and a background spectrum. The RF signal generation and detection module is also to remove the background spectrum from the transmission spectrum leaving an absorption line spectrum, wherein the removal of the background spectrum calibrates the spectrometer, to generate an error signal based on the absorption line spectrum, and to adjust the transmitted RF signals to lock-in on the absorption line spectrum.

BRIEF DESCRIPTION OF THE DRAWINGS

For a detailed description of exemplary embodiments of the invention, reference will now be made to the accompanying drawings in which.

NOTATION AND NOMENCLATURE

Figure 1:
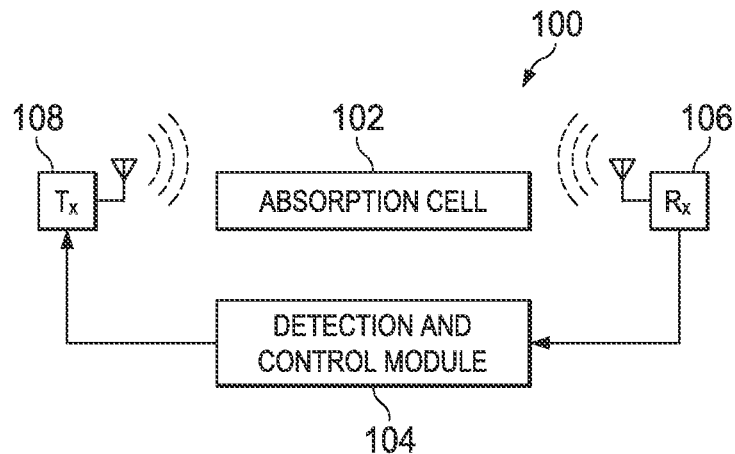
FIG. 1 shows a block diagram of a spectrometer 100 implementing a calibration and error correction scheme in accordance with various examples.

Certain terms are used throughout the following description and claims to refer to particular system components. As one skilled in the art will appreciate, companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . . " Also, the term "couple" or "couples" is intended to mean either an indirect or direct connection. Thus, if a first device couples to a second device, that connection may be through a direct connection, or through an indirect connection via other devices and connections.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Spectroscopic systems may require calibration to ensure the accuracy of the measurements and to calibrate the system. Calibrating the systems allows for adjusting measured spectrums to remove any inherent system characteristics that may adversely impact the measurements. Calibration may be performed at system start-up or periodically during run-time to ensure the fidelity of the measurements, but the calibration may require ancillary equipment, which may not lend itself to compact, portable spectroscopic systems.

When performing transmission spectroscopy, of a gas for instance, and searching for fine absorption details, a background spectrum may interfere with the analysis process by obscuring such fine absorption details. The background spectrum, as used herein, relates to performance characteristics of the measurement system, or more specifically, a spectrometer. To obtain the fine absorption details of interest without the noise of the background system, the removal of the background spectrum from the transmission spectrum may be helpful. Conventionally, to remove the background spectrum, a two-step process may be implemented. First, a spectrum is measured without the gas of interest in the system to obtain the background spectrum, i.e., the spectrum data characteristic of the system. Second, a transmission spectrum with the gas of interest in the system may then be measured. Alternatively, those two steps may be reversed. The background spectrum may then be removed from the measured transmission spectrum to obtain just the spectrum of the gas of interest. In general, the background spectrum and the measured transmission spectrum may need to be de-convolved, but subtraction may be conventionally performed due to the ease of the calculation.

After removal of the background spectrum, an absorption line of the gas of interest may be more easily analyzed and tracked by the spectroscopic system. To track the absorption line, however, feedback may be required so that the probing energy, radio frequency (RF) signals, for example, is continuously adjusted so that the absorption line is always being monitored by the spectroscopic system. As used herein, "locking-in on" or "tracking" (and their variations) may refer to the absorption line being continuously measured or monitored by the spectroscopic system so that the center frequency of the absorption line is known. The feedback may be in the form of an error signal that is fed into an RF generator that directs the frequency at which the RF signals are emitted.

Disclosed herein are systems and methods that enable the removal of a background spectrum from a measured transmission spectrum where the background spectrum is based on performance characteristics of a spectrometer system. The spectrometer may estimate the performance characteristics of a gas absorption cell and the performance characteristics of a detector. Those performance characteristics may then be combined with the measured transmission spectrum to remove the background spectrum from the measured transmission spectrum. The spectrometer may then use the measured transmission spectrum without the background spectrum to generate an error signal used for tracking or locking-in on a feature of the transmission spectrum.

FIG. 1 shows a block diagram of a spectrometer 100 implementing the calibration and error correction scheme in accordance with various examples. The spectrometer 100 may comprise a gas absorption cell 102 (cell 102), a detection and control module 104, a radio frequency (RF) receiver 106, and a RF transmitter 108. The cell 102 may contain a gas such as air or water vapor, which may exhibit characteristic absorption lines at various frequencies. The RF transmitter 108 may be coupled to the detection and control module 104 and may transmit RF signals into the cell 102. The RF signals transmitted into the cell 102 may be received as they exit the cell 102 by the RF receiver 106.

The detection and control module 104 may include many of the functions to implement the calibration and error correction scheme. The calibration process may be run at the start-up of the spectrometer 100 or the calibration process may be run periodically to ensure its accuracy. If the environmental conditions of the spectrometer 100 change, e.g. temperature and/or pressure of the cell 102, then the calibration process may be run periodically to account for such changes due to the effects the environmental factors may have on the spectrometer 100. Changes to the environmental factors may affect the background spectrum and the absorption line necessitating recalibration of the spectrometer 100. For example, if the cell 102 experiences an increase in temperature, the gas contained within may experience a corresponding increase in energy. The increase in energy may manifest itself in the measured spectrum in a broadening of the absorption line and changes in the background spectrum that may interfere with the measurement of the absorption line.

In addition to the cell 102, a detector included in the detection and control module 104 may also affect the background spectrum. The inherent performance characteristics of the detector may affect the background spectrum due to a direct current (DC) offset it may impart to the received signals and a characteristic responsivity. The responsivity of the detector may be a measure of the input-output gain of the detector.

To measure a transmission spectrum, the spectrometer 100 may implement various modulation schemes for measuring the spectrum. The spectrometer may use amplitude modulation (AM), frequency modulation (FM), or frequency-shift keying (FSK), for example, to assist with detection of the probing energy, the RF signals. If, for example, FSK is used, the detection and control module 104 may generate two distinct RF tones (Tone 1 and Tone 2) at different frequencies with the two tones being separated by a set frequency range, e.g., less than one megahertz. In general, the frequency separation of the two tones may be set to correspond to the line width of a desired absorption line. The two tones may then be alternately transmitted at a 50% duty cycle and, at system start up, swept across a range of frequencies to detect the absorption line of interest. The absorption line of interest may be deemed to be found when the difference between the received signals corresponding to the two tones is zero. For example, when the measured data at the frequency of Tone 2 minus the measured data at the frequency of Tone 1 is zero. This calculation may represent a rough detection of the absorption line, which may be refined when calibration data is used to compensate the measurement. Then, once the detection of the absorption line is refined, the error signal may be generated to lock-in on the absorption line.

Figure 2:
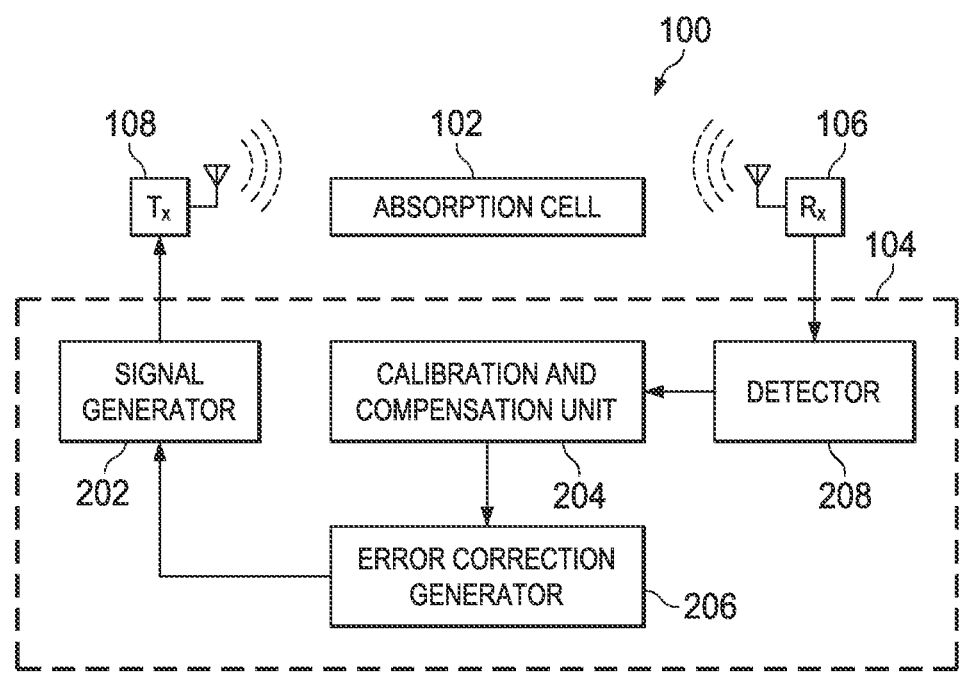
FIG. 2 shows another block diagram of the spectrometer 100 in accordance with various examples.

FIG. 2 shows a block diagram of a spectrometer 100 in accordance with various examples as discussed herein and to implement the calibration and error correction scheme. The spectrometer 100 is shown to include the same components as described in FIG. 1 with an expanded description of the detection and control module 104. The detection and control module 104 may further comprise a signal generator 202, a calibration and compensation unit 204, an error correction generation unit 206, and a detector 208. The signal generator 202 may be used to generate the RF signals transmitted by the RF transmitter 108. Further, the RF signal generator 202 may generate the two FSK tones discussed above.

The detector 208 may be coupled to the RF receiver 106 and the calibration and compensation unit 204. The detector 208 may measure the received signals from the two FSK tones and may use that information in the detection of an absorption line of the gas in the cell 102. The magnitude of the received signals corresponding to the two FSK tones may include both the signature information of the absorption line along with the background spectrum at those frequencies. In order for the calibration and compensation unit 204 to remove the background spectrum from the signal, the spectrometer 100 may initiate a calibration procedure. As noted, the calibration procedure may be run at system start up or periodically. The calibration procedure may involve estimating the performance characteristics of the cell 102 and the detector 208.

To estimate the performance characteristics of the cell 102, the calibration and compensation unit 204 may fit the measured spectrum in the vicinity of the absorption line with a low-order polynomial. When fitting the spectrum with the low-order polynomial, the unit 204 may ignore the absorption line so that the absorption line does not affect the polynomial.

In the case of a first-order polynomial, or straight line, this estimation process will result in a slope, m, and a y-intercept, b. These two values may be used to represent the performance characteristics of the cell 102.

To estimate the performance characteristics of the detector 208, which may be a detector such as an envelope detector or a square-law detector, the DC-offset and the detector's responsivity may be estimated. The DC-offset may be a measure of how much DC voltage the detector adds to the magnitude of the received RF signals. The DC-offset may also be determined by plotting output voltage versus input power and extrapolating back from the linear portion of this plot to the y-axis, which may be in units of voltage. The point at which this extrapolation crosses the y-axis may be the detector's DC-offset. The responsivity, may be a measure of the gain per input power of the detector 208 and my heuristically determined or input from the detector's data sheet.

Once the calibration values have been estimated, the subsequent measurements performed by the spectrometer 100 may be compensated to remove the background spectrum from the measurements. The following formula is a model of the measurement per frequency:

$$y(f) = R_v(mf+b)t(f)P_{in} + y_{DC} \quad \text{(Eq. 1)}$$

where $P_{in}$ is the power input to the absorption cell;

t(f) is the absorption line transmission and is assumed to be 1, i.e., no absorption, so the absorption line is not included in the measurement (i.e., it is not part of the calibration and compensation calculations);

m is the slope of the first-order polynomial fit to the measured spectrum;

b is the y-intercept of the first-order polynomial fit to the measured spectrum;

$y_{DC}$ is the DC-offset of the detector;

$R_v$ is the responsivity of the detector; and y(f) is the measured transmission at frequency f and includes the absorption line and the background spectrum.

Thus, the magnitude of the absorption line spectrum at the two FSK tones, Tone 1 and Tone 2, after compensation, i.e., removal of the background spectrum, becomes:

$$t(f_1) = [y(f_1) - y_{DC}] / [R_v(mf_1 + b)P_{in}] \quad \text{(Eq. 2)}$$

and $$t(f_2) = [y(f_2) - y_{DC}] / [R_v(mf_2 + b)P_{in}] \quad \text{(Eq. 3)}$$

where $f_1$ is FSK tone one, Tone 1, and $f_2$ is FSK tone two, Tone 2; and $y(f_1)$ is the DC-coupled measurement obtained by the detector 208 while Tone 1 is transmitting and $y(f_2)$ is the DC-coupled measurement obtained by the detector 208 while Tone 2 is transmitting. Thus, the compensated measurements taken at the two FSK tones are represented by $t(f_1)$ and $t(f_2)$.

The error correction generator 206 may be coupled to the calibration and compensation unit 204 and the signal generator 202. Once the absorption line of interest has been detected by the spectrometer 100, the error correction generator 206 may then continuously adjust the signal generator 202 to lock-in on the absorption line using the compensated values, $t(f_1)$ and $t(f_2)$. The center frequency between the two FSK tones may coincide with the center frequency of the absorption line when the absorption line is locked-in on by the spectrometer 100. In such a scenario, the frequency corresponding to the center frequency of the absorption line may be used as a reference frequency by other electronic components. The error signal may be calculated by the error correction generator 206 and may be represented by subtracting Eq. 2 from Eq. 3, i.e., $t(f_2) - t(f_1)$. The result of this computation may represent the desired error signal and may be in units of voltage. A scaling factor may be required to convert the error signal from units of voltage to units of frequency so the signal generator 202 may be adjusted.

Figure 3:
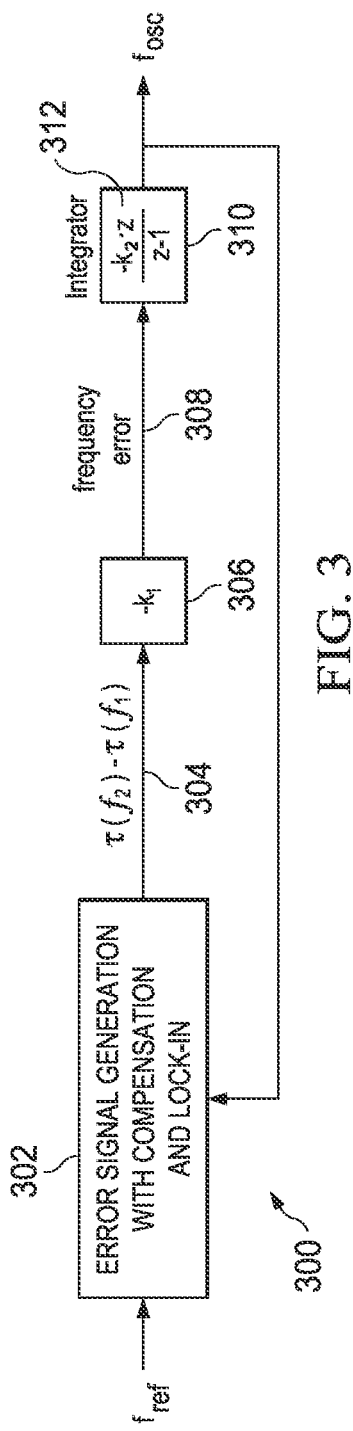
FIG. 3 shows a block diagram of the control system representing the implementation of the error signal in accordance with various examples and to produce an oscillator frequency equal to the center frequency of the absorption line.

FIG. 3 shows a block diagram of the control system representing the implementation of the error signal in accordance with various examples and to produce an oscillator frequency equal to the center frequency of the absorption line. The control system 300 may comprise an error signal generation with compensation and lock-in block 302, a conversion block 306, and an integrator block 312. The control system 300 depicts $f_{ref}$ as an input on the left side. The $f_{ref}$ notation may represent a reference frequency the control system is attempting to track so that the frequency, $f_{OSC}$, equals $f_{ref}$. The frequency $f_{ref}$ may be the center frequency of an absorption line being detected and tracked by the spectrometer 100. For example, if the gas in the cell 102 is water vapor, then $f_{ref}$ may correspond to the frequency of a 183.31 GHz absorption line of water.

The block 302 may be the error signal generator 206 or the combination of the calibration and compensation unit 204 and the error signal generator 206. The output of the block 302 may be the difference between $f_{OSC}$ and $f_{ref}$, which may be zero when they equal but may be $t(f_2) - t(f_1)$ 304 when they are not equal. The error signal $t(f_2) - t(f_1)$ 304 may correspond to the output of the error generator 204. The error signal $t(f_2) - t(f_1)$ 304 may represent the difference between the center frequency of the absorption line being measured and the mid-point between the two FSK tones, Tone 1 and Tone 2. As such, the control system 300 may be used to drive the center frequency between the two tones to equal the center frequency of the absorption line. However, as noted above, the units of $t(f_2) - t(f_1)$ may be in volts. Thus, a conversion factor may be used to convert the error signal in volts to Hz so that the signal generator 202 may be adjusted. The conversion factor is represented by $k_1$ 306, which may convert the error signal $t(f_2) - t(f_1)$ from volts to the frequency error 308 in units of Hz.

The integrator 310 includes another factor, $k_2$ 312, which may be the inverse of $k_1$ 306. By configuring k2 312 to be the inverse of k1 306, the response time of the integrator 310 may be at a maximum so that that spectrometer 100 responds to changes in the center frequency of the absorption line with little delay resulting in a steady value for $f_{OSC}$.

Figure 4:
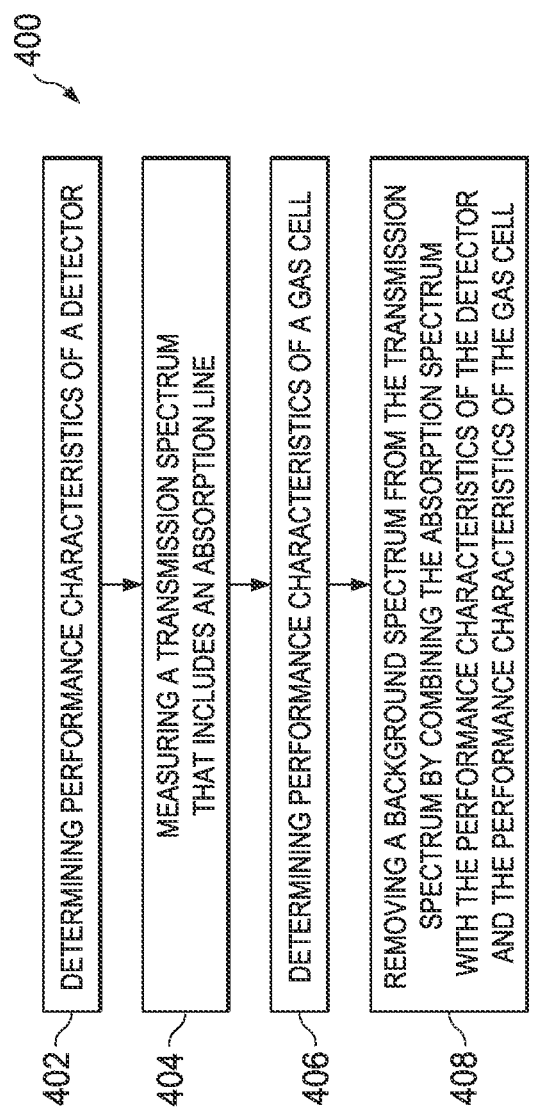
FIG. 4 is a flow chart for a method 400 used to implement the calibration and compensation scheme in accordance with various examples discussed herein.

FIG. 4 is a flow chart for a method 400 used to implement the calibration and compensation scheme in accordance with various examples discussed herein. The method 400 begins at step 402 with determining performance characteristics of a detector, such as the detector 208. The performance characteristics of the detector 208 may include the responsivity and the DC-offset of the detector 208. The method 400 continues at step 404 with measuring a transmission spectrum that includes an absorption line. The method 400 continues at step 406 with determining the performance characteristics of a gas cell, such as the cell 102. The performance characteristics of the cell 102 may be determined by fitting a measured spectrum in the vicinity of an absorption line with a low-order polynomial. The slope and y-intercept of the first-order polynomial may represent the performance characteristics of the cell 102.

The method 400 then ends at step 408 with removing a background spectrum from the transmission spectrum by combining the absorption spectrum with the performance characteristics of the detector and the performance characteristics of the gas cell. By combining the performance characteristics of the gas cell, such as cell 102, and the detector, such as the detector 208, with the measured transmission spectrum, the background spectrum may be removed from the measured spectrum leaving the transmission spectrum of the gas in the cell 102. The combination of the transmission spectrum and the performance characteristics may be implemented using Eq. 2 and Eq. 3 above. Thus, implementing those two equations may allow the spectrometer 100 to continuously compensate the measurements made at the two FSK tones, Tone 1 and Tone 2.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A method for removing the background from a transmission spectrum, comprising:
   determining performance characteristics of a detector;
   measuring a transmission spectrum that includes an absorption line;
   determining performance characteristics of a gas cell; and
   removing a background spectrum from the transmission spectrum by combining the transmission spectrum with the performance characteristics of the detector and the performance characteristics of the gas cell.

2. The method of claim 1, wherein determining the performance characteristics of the detector comprises estimating a responsivity and a DC-offset of the detector.

3. The method of claim 2, wherein combining comprises subtracting the DC-offset from the transmission spectrum.

4. The method of claim 3, wherein combining further comprises: at a frequency, computing a quotient of the transmission spectrum without the DC-offset to the product of the responsivity, the characteristics of the gas cell, and an input power value, wherein the result of the quotient is the transmission spectrum without the background spectrum at the frequency.

5. The method of claim 1, wherein determining the performance characteristics of the gas cell comprises fitting the transmission spectrum in the vicinity of the absorption line with a polynomial, the performance characteristics of the gas cell are represented by the slope and y-intercept of the polynomial.

6. The method of claim 1 further comprising determining edge frequencies of the absorption line, wherein the edge frequencies correspond to a point of maximum slope of the transmission spectrum of the absorption line.

7. The method of claim 6, further comprising computing the quotient for the edge frequencies of the absorption line.

8. The method of claim 7, further comprising computing the difference between the quotients for the two edge frequencies wherein the difference between the quotients for the two edge frequencies is an error signal.

9. The method of claim 8, wherein the error signal is used to track the absorption line.

10. A system for removing a background spectrum from a measured spectrum, comprising:
    an absorption cell containing a gas;
    a radio frequency (RF) transmitter to transmit a RF signal through the absorption cell;
    a detector to receive the RF signal; and
    a control module coupled to the transmitter and the detector to:
       estimate performance characteristics of the detector and performance characteristics of the gas cell;
       measure a transmission spectrum of the gas in the absorption cell; and
       combine the transmission spectrum with the performance characteristics of the gas cell and the detector to remove a background spectrum from the transmission spectrum.

11. The system of claim 10, wherein the control module locks-in on an absorption line of the transmission spectrum.

12. The system of claim 10, wherein the control module estimates the performance characteristics of the gas cell by fitting the transmission spectrum in the vicinity of the absorption line with a polynomial, wherein a slope and a y-intercept of the polynomial represent the performance characteristics of the gas cell.

13. The system of claim 12, wherein the control module determines a responsivity and a DC-offset of the detector to estimate the performance characteristics of the detector.

14. The system of claim 13, wherein the control module subtracts the DC-offset from the transmission spectrum then divides the result of the subtraction by a product of the responsivity, the performance characteristics of the gas cell, a frequency, and an input power to remove the background spectrum from the transmission spectrum at that frequency.

15. The system of claim 14, wherein the control module determines edge frequencies of the transmission line spectrum of the absorption line, and the edge frequencies correspond to a point of maximum slope of the transmission spectrum of the absorption line.

16. The system of claim 15, wherein the control module removes the background spectrum from the transmission spectrum at the edge frequencies of the absorption line.

17. The system of claim 16, wherein the control module generates an error signal by taking the difference of the transmission spectrums without the background spectrum for the edge frequencies.

18. A spectrometer, comprising:
    an absorption cell containing a gas;
    a radio frequency (RF) transmitter to transmit RF signals into the absorption cell;
    a RF receiver to receive the RF signals; and
    a RF signal generation and detection module coupled to the transmitter and the receiver to:
       generate the RF signals;
       detect the RF signals received by the receiver;
       measure a transmission spectrum based on the received RF signals, wherein the measured transmission spectrum includes an absorption line of the gas and a background spectrum;
       remove the background spectrum from the transmission spectrum leaving an absorption line spectrum, wherein the removal of the background spectrum calibrates the spectrometer;
       generate an error signal based on the absorption line spectrum; and
       adjust the transmitted RF signals to lock-in on the absorption line spectrum.

19. The device of claim 18, wherein the RF signals are two frequency-shift keying (FSK) modulation tones.

20. The device of claim 19, wherein the error signal is a difference between an absorption spectrum value at the two FSK modulation tones calculated after the background spectrum has been removed.

21. The device of claim 18, wherein the background spectrum is a combination of performance characteristics of the absorption cell and of the RF signal generation and detection module.

22. The device of claim 21, wherein the RF signal generation and detection module fits the absorption line spectrum with a polynomial and the slope and y-intercept of the polynomial represent the performance characteristics of the absorption cell.

23. The device of claim 21, wherein the RF signal generation and detection module performance characteristics are estimates of a responsivity and a DC-offset.

* * * * *